United States Patent
Grimaldi

(10) Patent No.: US 8,784,296 B2
(45) Date of Patent: Jul. 22, 2014

(54) ANGLED SURGICAL INTRODUCER

(75) Inventor: John Grimaldi, Lawrenceville, IL (US)

(73) Assignee: Coloplast A/S, Humlebaek (DK)

(*) Notice: Subject to any disclaimer, the term of this patent is extended or adjusted under 35 U.S.C. 154(b) by 114 days.

(21) Appl. No.: 13/226,840

(22) Filed: Sep. 7, 2011

(65) Prior Publication Data

US 2012/0065459 A1 Mar. 15, 2012

Related U.S. Application Data

(60) Provisional application No. 61/380,415, filed on Sep. 7, 2010.

(51) Int. Cl.
*A61F 2/02* (2006.01)

(52) U.S. Cl.
USPC .......................................................... 600/30

(58) Field of Classification Search
CPC ... A61F 2/0004; A61F 2/0031; A61F 2/0045; A61F 2/0063; A61F 2017/00805; A61B 17/06066
USPC .............. 600/30, 37; 606/151, 222–236, 144, 606/148, 187; 623/23.64; 66/63, 118, 14; 112/80.15
See application file for complete search history.

(56) References Cited

U.S. PATENT DOCUMENTS

| | | | |
|---|---|---|---|
| 4,566,446 A | 1/1986 | Fogarty | 600/40 |
| 4,583,540 A * | 4/1986 | Malmin | 606/187 |
| 4,982,731 A | 1/1991 | Lue et al. | 600/40 |
| 5,059,207 A * | 10/1991 | Shah | 606/223 |
| 5,062,417 A | 11/1991 | Cowen | 600/40 |
| 5,163,897 A | 11/1992 | Persky | 600/31 |
| 5,250,020 A | 10/1993 | Bley | 600/40 |
| 5,634,878 A | 6/1997 | Grundei et al. | 600/30 |
| 5,851,176 A | 12/1998 | Willard | 600/40 |
| 5,895,424 A | 4/1999 | Steele, Sr. et al. | 600/40 |
| 6,129,741 A * | 10/2000 | Wurster et al. | 606/222 |
| 6,171,233 B1 | 1/2001 | Willard | 600/40 |
| 6,387,071 B1 * | 5/2002 | Constantz | 604/43 |
| 6,502,578 B2 | 1/2003 | Raz et al. | 128/898 |
| 6,786,861 B1 | 9/2004 | Pretorius | 600/31 |
| 7,273,448 B2 | 9/2007 | Arnal et al. | 600/30 |
| 7,395,822 B1 | 7/2008 | Burton et al. | 128/885 |
| 7,422,557 B2 | 9/2008 | Arnal et al. | 600/30 |
| 7,431,690 B2 | 10/2008 | Merade et al. | 600/30 |
| 7,608,067 B2 | 10/2009 | Bonni | 604/323 |
| 7,611,454 B2 | 11/2009 | De Leval | 600/30 |
| 7,621,864 B2 | 11/2009 | Suslian et al. | 600/30 |

(Continued)

FOREIGN PATENT DOCUMENTS

| | | |
|---|---|---|
| DK | 2009 00718 | 12/2010 |
| WO | WO 98/31301 | 7/1998 |

(Continued)

*Primary Examiner* — Jacqueline Cheng
*Assistant Examiner* — Kaylee Wilson
(74) *Attorney, Agent, or Firm* — Coloplast Corp., Coloplast A/S; Nick Baumann

(57) ABSTRACT

The invention describes a surgical introducer comprising a proximal tip portion and a distal tip portion, wherein each tip portion comprises a notch, a base portion comprising an angle, wherein the base portion is between the proximal tip portion and the distal tip portion and wherein the base portion is wider than the remainder of the introducer. The introducer can be used for insertion of arms of a urethral sling into a patient.

12 Claims, 1 Drawing Sheet

(56) References Cited

U.S. PATENT DOCUMENTS

| | | | |
|---|---|---|---|
| 2001/0023356 A1 | 9/2001 | Raz | 128/989 |
| 2002/0147382 A1* | 10/2002 | Neisz et al. | 600/29 |
| 2004/0215054 A1 | 10/2004 | Siegel | 600/31 |
| 2005/0143618 A1* | 6/2005 | Anderson et al. | 600/29 |
| 2005/0283040 A1 | 12/2005 | Greenhalgh | 600/30 |
| 2006/0052800 A1 | 3/2006 | Greenhalgh | 600/30 |
| 2006/0122457 A1 | 6/2006 | Kovac | 600/37 |
| 2006/0224039 A1 | 10/2006 | Steele | 600/38 |
| 2007/0049790 A1 | 3/2007 | Wagner | 600/30 |
| 2007/0055095 A1* | 3/2007 | Chu et al. | 600/37 |
| 2007/0106897 A1 | 5/2007 | Kulakowski | 455/411 |
| 2007/0142700 A1 | 6/2007 | Fogarty | 600/40 |
| 2010/0191038 A1* | 7/2010 | Kubalak et al. | 600/30 |
| 2010/0197998 A1 | 8/2010 | Comiter | 600/30 |

FOREIGN PATENT DOCUMENTS

| | | | |
|---|---|---|---|
| WO | WO 2004/096087 | 11/2004 | |
| WO | WO 2005/009293 | 2/2005 | |
| WO | WO 2006/012653 | 2/2006 | |
| WO | WO 2008048971 A2 * | 4/2008 | A61B 5/00 |

* cited by examiner

ANGLED SURGICAL INTRODUCER

CROSS REFERENCE TO RELATED APPLICATIONS

This application claims priority to U.S. Provisional Patent Application Ser. No. 61/380,415 filed Sep. 7, 2010. This provisional application is expressly incorporated by reference.

FIELD OF THE INVENTION

The invention relates generally to a novel dual tipped, angled surgical needle suitable for use in inserting a urethral support into an individual in need thereof.

BACKGROUND OF THE INVENTION

Urinary incontinence is a condition characterized by involuntary loss of urine beyond the individual's control. One cause for this loss of control is damage to the urethral sphincter caused by, for example, prostatectomy, radiation therapy or pelvic accidents. Other causes of incontinence include bladder instability, over-flowing incontinence and fistulas.

Current approaches to alleviate the incontinence include prostheses, such as slings, that exert a force on the urethra to prevent unintentional voiding of the bladder or artificial sphincters. Simply, the sling (whether it be two armed or more) is secured to the patient's tissue such that the urethra is supported by the sling. The sling applies pressure to the urethra to prevent unwanted discharge of urine.

One approach provides an artificial sphincter that has an inflatable cuff that fits circumferentially around the urethra near where the urethra joins the bladder. A balloon regulates cuff pressure and a bulb controls inflation and deflation of the cuff. The balloon is surgically placed within the pelvic area, and the control pump is placed in the scrotum.

The cuff is inflated to keep urine from leaking. When urination is desired, the cuff is deflated, allowing urine to drain out.

Urethral slings include those disclosed, for example, in U.S. Pat. Nos. 7,621,864, 7,611,454, 7,431,690 and 7,422,557 and U.S. Patent Publication Nos. 2005/0283040, 2006/0052800, 2006/0122457, and US 2010/0197998, the contents of which are included in their entirety.

Inflatable balloons are also known in the art. They can be used in connection with erectile dysfunction or with urethral prostheses. Suitable inflatable balloon technology includes that disclosed in U.S. Pat. Nos. 4,566,446, 5,062,417, 5,250,020, 5,851,176, 5,895,424, 6,171,233 and 4,982,731 and U.S. Patent Publication Nos. 2006/224039, 2007/0142700 and 2007/106897, the contents of which are included in their entirety.

Artificial sphincters are disclosed in PCT Publication Nos. WO 2005/009293, WO 2006/012653, WO 2004/096087 and WO 98/31301 and U.S. Pat. Nos. 5,163,897, 5,634,878 and 6,786,861, the contents of which are included in their entirety.

Combinations of slings with inflatable balloons are also known in the art. They include those disclosed in Danish application PA 2009 00718, filed Jun. 8, 2009, entitled "Anatomical Augmentation Device", U.S. Pat. Nos. 7,395,822, 6,786,861, 7,395,822, 7,608,067 and 7,273,448 and U.S. Patent Publication Nos. 2004/0215054 and 2007/0049790, the contents of which are included in their entirety.

For example, a fluid filled chamber is incorporated into the prosthesis to provide improved treatment of incontinence. U.S. Pat. No. 6,502,578 and U.S. Published Patent Application 2001/0023356, report an apparatus and method for treatment of male incontinence in which a "hammock-like" prosthesis is positioned between the descending rami of the pubic bone. The prosthesis includes an inflatable balloon device positioned to provide passive compression on the bulbar urethra to prevent voiding of the bladder. The volume of the balloon may be adjusted after implantation in a patient with a introducer and syringe device.

Suitable slings may include a Virtue® male sling (Coloplast Corp., 601 West River Road North, Minneapolis, Minn. 55411) which comprises two transobturator arms and two prepubic arms. In known techniques, a J-hook needle is required to place the transobturator arms of the sling. This same needle is often used for the tunneling technique to place the prepubic arms of the sling. If the J-hook needle is not used, a tonsil clamp is often recommended for the tunneling of both the transobturator arms and prepubic arms. The prepubic arms of a sling are placed about 10 cm apart from one another, about 5 cm from the midline in the patient's prepubic region.

One disadvantage that arises from the current process is the tunneling required between the prepubic arms. When the prepubic arms are spaced about 10 cm apart it becomes difficult to pass the J hook needle. An instrument such as a tonsil clamp must then be used to pass through the subcutaneous tissues, from the first prepubic incision to the second prepubic incision. This is then repeated for the other prepubic arm from the second prepubic incision to the first prepubic incision.

Other techniques may use a Stamey needle (Cook Medical, Bloomington, Ind. 47402-4195) or a Raz needle (Cook Medical, Bloomington, Ind. 47402-4195) instead of a J hook needle and tonsil clamp. A Stamey or Raz needle may be placed through the prepubic incision and guided out through the perineal incision on the ipsilateral side. The traction sutures from this side are then attached to the needle and withdrawn in the reverse process. The process is then repeated for the contralateral side. Once the prepubic arms are in place and the tensioned properly, the arms need to be tunneled in a crossover fashion. The needle is placed in the prepubic incision and tunneled to the opposite prepubic incision. The sling is attached to the needle and withdrawn. The procedure is then reversed for the contralateral side.

Alternatively, a "one pass" tunneling technique for the prepubic arms has been developed. After the prepubic arms have been placed and tensioned, the Raz or Stamey needle is attached to the ipsilateral traction suture of the sling. The needle is passed in a "cross-over" fashion. The traction suture is removed and the traction suture is attached to the needle, and this needle is withdrawn. Now, both arms are placed and only one pass of the needle has been used. This decreases the amount of tissue damage and greatly reduces intraoperative times. Using this technique, the procedure can be completed in 20 minutes or less.

A looped suture is currently attached to all four arms of the sling through a hole in the tip of a Stamey or Raz needle. On a Raz needle, the looped suture from the Virtue male sling is easily passed through this aperture. This loop is then placed over the tip of the needle and pulled tight in a "slip knot" fashion. On a Stamey needle, the hole present on the end is too small to accept the looped suture from the sling.

The needle may then be passed, initially, from the prepubic incision and guided through the perineal incision. Both the Stamey and Raz needle have a wide handle used to grasp. Although these handles make the needles easy to grasp and manipulate, they cannot be passed completely through the incision without significant tissue dissection and trauma. This makes the "top-down" approach necessary.

BRIEF SUMMARY OF THE INVENTION

The invention relates generally to a dual tipped, angled surgical needle or introducer suitable for use in inserting a urethral support into an individual in need thereof. In some embodiments, a surgical introducer is disclosed comprising: a base portion comprising a proximal tip portion and a distal tip portion, wherein each tip portion comprises a notch; and wherein the base portion between the proximal tip and distal tip is angled and is wider than the remainder of the introducer.

In certain embodiments, the base portion may be planar or tubular. Tip portions may be flattened prior to the endpoint of the needle or introducer. The base portion may be approximately midway between the proximal tip portion and the distal tip portion. The angle of the base portion may be between about 15 and about 30 degrees from a horizontal plane.

In various embodiments of the surgical needle or introducer, the length of the surgical or introducer may be between about 15 to about 25 cm in length. The notch may be a T-slot or an L-slot.

In other embodiments, a method to secure a four-armed urethral sling is presented, the method comprising the steps: positioning a first pair of arms of a four-armed urethra sling to suitable sites in the left and right transobturators; and positioning a second pair of arms of the four-armed urethral sling to suitable sites through the abdominal wall suprapubicly, wherein a portion of the second pair of arms is guided through the tissue via a surgical needle or introducer comprising a base portion comprising a proximal tip portion and a distal tip portion, wherein each tip portion comprises a notch; and wherein the base portion between the proximal tip and distal tip is angled and is wider than the remainder of the needle or introducer.

The present invention also provides methods to secure a urethral prosthesis including a four-armed urethral sling having a support portion, such as that described in U.S. Pat. No. 7,431,690 and/or in U.S. Patent Pub. No. 2010/0197998. The method can include the use of the dual tipped, angled surgical needed described herein. The urethral prosthesis can be implanted such that the unintentional leakage from a patient's bladder is prevented.

The term "coupled" is defined as connected, although not necessarily directly, and not necessarily mechanically.

The terms "a" and "an" are defined as one or more unless this disclosure explicitly requires otherwise.

The term "substantially" and its variations (e.g. "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of what" is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features.

Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of:"

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art.

Nothing herein is to be construed as an admission that the invention is not entitled to antedate such disclosure by virtue of prior invention.

Figure 1:
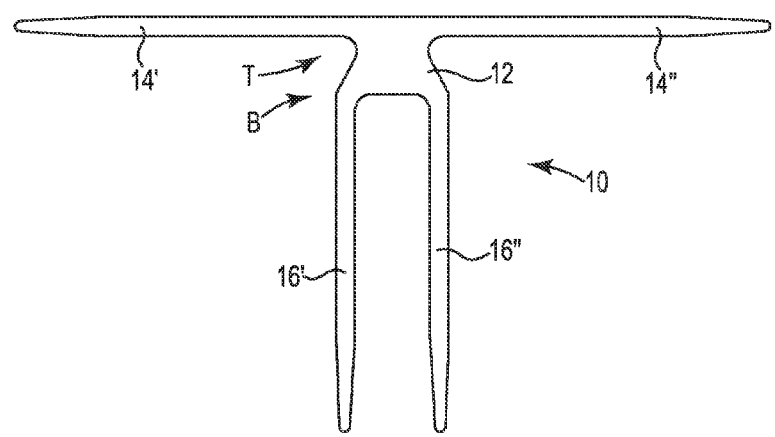
FIG. 1 illustrates one of the present embodiments of an implantable urethral sling.

One embodiment of a urethral prosthesis is an implantable sling 10 (or, "sling 10"). Embodiments of sling 10 as contemplated for use with the present needle or introducer 20 is illustrated in FIG. 1. Sling 10 comprises a body member 12, a first elongated extension member 14', a second elongated extension member 14", a third elongated extension member 16', and a fourth elongation extension member 16". First elongated extension member 14' and second elongated extension member 14" are also called "transobturator arms 14". Third elongated extension member 16' and fourth elongation extension member 16" are also called "prepubic arms 16." These components are placed in such an orientation as to provide both anchoring and support to the bulbar urethral complex of a male patient.

In one embodiment, the body member 12 may be formed substantially in the shape of a trapezoid. Prepubic arms 14 extend from a top T of the trapezoidal body member 12 and the transobturator arms 16 extend from a bottom B of the trapezoidal body member 12. It is to be understood, however, that prepubic arms 16 may be in any orientation with respect to each other, whether parallel, substantially so, or not parallel at all. Ultimately, orientation of prepubic arms 16 may be chosen with respect to suitability for each patient's unique anatomy. In summary, The angles and dimensions of the trapezoidal body member 12 may vary depending on the type of material and on the particular anatomy of the patient receiving the device. Thus it should be understood that the tapering end (top) T of the trapezoid, from where transobturator arms 14 extend, should fit between the pubic rami. In this regard, it will be appreciated that if the width of the tapering end exceeds a width between the pubic rami, then there is a risk that the material of sling 10 could fold, bulge, or otherwise deform and thus compromise the success of the surgery as described above. However, the widest end of the trapezoid (bottom) B of the body member 12 serves to support the bulbar urethral complex; thus, the larger surface (relative to the top of the trapezoid) evenly distributes pressure and provides a desirable compression of the urethral complex.

Materials suitable for use in constructing sling 10 of the present invention may include synthetic materials such as meshes and the like, natural tissues such as tissues harvested from an animal, a cadaverous source, or the patient himself, or any suitable combinations of synthetic and natural materials.

Sling 10 illustrated in FIG. 1 may be, for example, fabricated from a mesh. The mesh may be warp knitted from 7.5 mil monofilament polypropylene. Table 1 shows example specifications of such a mesh formed in accordance with sling 10 illustrated in FIG. 1.

TABLE 1

| | |
|---|---|
| WPI | 17 |
| CPI | 41 |
| Thickness | 0.0251" |
| Density | 146.3 (g/m2) |
| Pore Size | 0.4419 (mm2) |
| Burst Strength | 149.991 (lbf) |
| Tensile strength, Machine Direction | 92.608 (lbf) |
| Tensile strength, Cross Direction | 90.894 (lbf) |
| Stiffness, Machine Direction | 2.91 (cm) |
| Stiffness, Cross Direction | 3.70 (cm) |

Embodiments of the Present Surgical Needle or Introducer

Figure 2:
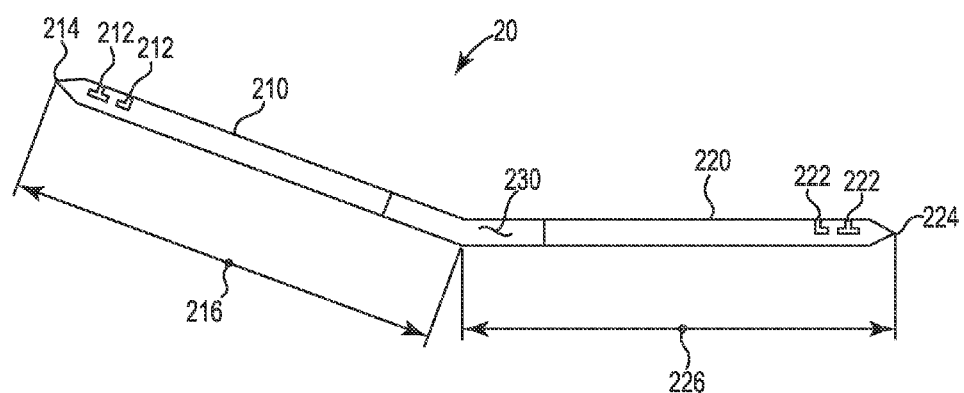
FIG. 2 illustrates one of the present embodiments of a dual tipped needle or introducer of the invention.

FIG. 2 illustrates one of the present embodiments of a surgical needle or introducer 20 configured for use with sling 10.

Needle or introducer 20 comprises a first leg 210 comprising a first length 216 and a second leg 220 comprising a second length 226. Lengths 216, 226 of each leg 210, 220 may be between about 7.5 cm and about 12.5 cm in various embodiments. Thus, needle or introducer 20 may have an overall length of between about 15 cm and about 25 cm.

The term needle is intended to mean a unitary structure having a substantially uniform diameter along the length of the needle 20. Generally the diameter is from about ¼ inches to about ¾ inches, more particularly about ⅜ inches.

The term introducer is meant to encompass a member having a first leg 210 and a second leg 220 that can be flat, octagonal, triangular, square, etc. and not necessarily round like that of a needle as described above. Generally the width of first leg 210 and second leg 220 is from about ¼ inches to about 1 inches, more particularly from about ½ inches to about ¾ inches and most particularly about ½ inch. The thickness of first leg 210 and second leg 220 can be similarly proportioned to that of the width of the member.

Needle or introducer 20 comprises a proximal tip portion 214 and a distal tip portion 224. Tip portions 214, 224 may be flat (or flattened) prior to the endpoint of the needle or introducer. Proximal tip portion 214 comprises a first notch 212, and distal tip portion 224 comprises a second notch 222. Notches 212, 222 may be substantially "T-shaped" or substantially "L-shaped" in various embodiments. In the illustrated embodiment, notches 212, 222 are substantially T-shaped. In certain embodiments, tip portions 214, 224 may comprise both an L-shaped notch and a T-shaped notch.

Needle or introducer 20 further comprises a base portion 230 where first leg 210 and second leg 220 of needle or introducer 20 are joined. In the illustrated embodiment, base portion 230 comprises an angle such that needle or introducer 20 is angled at or around its midpoint. The angle is between about 15° and about 30° from a horizontal plane (i.e., the obtuse angle between first leg 210 and second leg 220 is between about 150° and about 165° in one plane).

In some embodiments, base portion 230 may have a diameter that is larger than the diameter of either leg 210 or leg 220. In other embodiments, base portion 230 may be greater in at least one dimension than legs 210 or 210 than the rest of needle or introducer 20.

In certain embodiments base portion 230 may be flattened (e.g., is substantially elliptical or substantially planar instead of being substantially round) and/or textured to improve grip. In such embodiments, base portion 230 may be wider than legs 210, 220 but may be shorter than legs 210, 220.

In other embodiments, base portion 230 may be tubular (e.g., may be hollow or solid with a substantially circular cross-section). In such embodiments, diameter of base portion 230 may be greater than diameter of legs 210, 220 such that base portion 230 is thicker than legs 210, 220 in any direction.

The needle or introducer can be fabricated from metals, such as stainless steel, or various polymers such as polyurethanes, polypropylenes, polyethylenes and the like. The material need not be limiting as long as the end tips are sharpened to degree to puncture tissue and provide the surgeon with enough rigidity to guide the needle or introducer through the tissue area.

Embodiments of Methods of Using the Present Surgical Needle or Introducer

Embodiments of the present needle or introducer 20 allow for a complete pass-through technique to be used. Needle or introducer 20 may be passed in a "top-down" approach, or alternatively, needle or introducer 20 may be attached to the traction sutures from sling 10 and passed from a perineal incision out through the target in the prepubic location. Once passed in this fashion, the needle or introducer can be left attached to sling 10 and is ready for the "cross-over" passage in the tunneling procedure for prepubic arms 16. It will be apparent to one skilled in the art that any references to placing an arm also include placing a portion of an arm.

A patient is placed in dorsal lithotomy position. A catheter is placed and the bladder is drained. The catheter is palpated and the site for the incision is selected on the patient's perineum. A small 2 cm incision at the level of the urethral bulb is preferred where the catheter cannot be palpated.

The incision is carried down through the superficial tissues to expose the subcutaneous fat (an extension of Colle's fascia). A combination of blunt dissection and electrocautery are then used to expose the bulb of the urethra and the bulbocavernosus muscle. The central tendon is exposed and taken down only until there is sufficient mobility of the urethra. The entire tendon is not resected up to the pelvic diaphragm.

Transobturator arms 14 of sling 10 are then placed using a J hook needle. One transobturator arm 14 is attached to the J hook needle with stay sutures. The tip of the J hook needle is then placed proximal to the level of the urethral bulb approximately 2 cm distal to the apex of the urogenital triangle. The J hook needle is then passed and delivered through the obturator foramen. The exit point of the J hook needle is at the junction of the thigh and the scrotum, below the adductor tendon. The J hook needle is then passed at an approximately 45° angle. The other transobturator arm 14 is then placed in substantially the same manner that the first arm was placed.

Next, prepubic arms 16 are implanted. Two small incisions are placed in the prepubic area, about 5 cm lateral to the midline and about 10 cm apart from one another. The incisions are placed where sling 10 falls comfortably when reflected on to the abdomen.

Needle or introducer 20 may then be inserted one of two ways. Needle or introducer 20 may be introduced into the perineal incision and out the prepubic incision, or needle or introducer 20 may be introduced into the prepubic incision and out the perineal incision. Needle or introducer 20 is passed anterior to the pubic bone. A suture loop of prepubic arm 16 is attached to either notch 212 or notch 222 of needle or introducer 20, and sling 10 is then pulled out either the prepubic incision (if needle or introducer 20 was first introduced into the perineal incision) or the perineal incision (if needle or introducer 20 was first introduced into the prepubic incision) such that needle or introducer 20 makes a complete pass through the patient. This step is then repeated for the other prepubic arm 16.

Transobturator arms 14 are tensioned laterally (e.g., by pulling on the arms) to elevate the bulbous urethra. Prepubic arms 16 are tensioned superiorly in the same manner to compress the bulbous urethra. The transobturator arms 14 and prepubic arms 16 are alternately tensioned until sling 10 is properly placed in the patient.

The Grimaldi needle or introducer 20 can be used to place the sling through a single perineal incision. The currently available methods, prior to the invention, involve a perineal incision and two "prepubic" incisions.

The present invention can be done entirely from the perineum providing the advantage of less incisions.

The needle allows for tensioning of the sling from "below". In other words, the prepubic arms do not need to be tensioned from the prepubic incisions. Rather, the prepubic arms can be attached to the Grimaldi needle and advanced. This allows for placement and applying the proper tension in the sling. At this point, the sling can be tensioned and fixated to the bone with the various techniques that are currently available.

The following paragraphs enumerated consecutively from 1 through 9 provide for various aspects of the present invention. In one embodiment, in a first paragraph (1.), a surgical needle or introducer is presented comprising: a proximal tip portion and a distal tip portion, wherein each tip portion comprises a notch; a base portion comprising an angle, wherein the base portion is between the proximal tip portion and the distal tip portion and wherein the base portion is wider than the remainder of the needle or introducer.

2. The surgical needle or introducer of paragraph 1, wherein the base portion is planar.

3. The surgical needle or introducer of paragraph 1, wherein the base portion is tubular.

4. The surgical needle or introducer of any of paragraphs 1 through 3, wherein the tip portions are flattened prior to the endpoint of the needle or introducer.

5. The surgical needle or introducer of any of paragraphs 1 through 4, wherein the angle portion is approximately mid way between the proximal tip portion and the distal tip portion.

6. The surgical needle or introducer of any of paragraphs 1 through 5, wherein the angle is approximately between about 15 and about 30 degrees from a horizontal plane.

7. The surgical needle or introducer of any of paragraphs 1 through 6, wherein the length of the surgical needle or introducer is between about 15 to about 25 cm in length.

8. The surgical needle or introducer of any of paragraphs 1 through 7, wherein the notch is a T-slot or an L-slot.

9. A method to secure a four-armed urethral sling comprising the steps: positioning a first pair of arms of a four-armed urethra sling to suitable sites in the left and right transobturators; and positioning a second pair of arms of the four-armed urethral sling to suitable sites through the abdominal wall suprapubicly, wherein a portion of the second pair of arms is guided through the tissue via a surgical needle or introducer as in any of paragraphs 1 through 8.

10. A kit comprising a surgical needle or introducer comprising: a proximal tip portion and a distal tip portion, wherein each tip portion comprises a notch; a base portion comprising an angle, wherein the base portion is between the proximal tip portion and the distal tip portion and wherein the base portion is wider than the remainder of the needle or introducer; and instructions for use of the needle or introducer.

11. The kit of paragraph 10, wherein the instructions include a method to secure a four-armed urethral sling comprising the steps: positioning a first pair of arms of a four-armed urethra sling to suitable sites in the left and right transobturators; and positioning a second pair of arms of the four-armed urethral sling to suitable sites through the abdominal wall suprapubicly, wherein a portion of the second pair of arms is guided through the tissue via a surgical needle or introducer as in any of paragraphs 1 through 8.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A surgical introducer for positioning a urethral sling comprising:
   a proximal tip portion and a distal tip portion, wherein each tip portion comprises a T-shaped slot configured to receive a suture loop;
   a base portion comprising exactly one angle at approximately the midpoint of the introducer, wherein the base portion is between the proximal tip portion and the distal tip portion, wherein the exactly one angle displaces the proximal tip portion out of a plane parallel with the distal tip portion, wherein the exactly one angle is acute as measured from the horizontal plane parallel with the distal tip portion to the outside of the proximal tip portion, wherein the base portion is wider than the remainder of the introducer, and wherein the width of the introducer is from about ¼ inches to about 1 inch.

2. The surgical introducer of claim 1, wherein the base portion is planar.

3. The surgical introducer of claim 1, wherein the base portion is tubular.

4. The surgical introducer of claim 1, wherein the tip portions are flat.

5. The surgical introducer of claim 1, wherein the angle is approximately between about 15 and about 30 degrees from a horizontal plane.

6. The surgical introducer of claim 1, wherein the length of the surgical introducer is between about 15 cm to about 25 cm in length.

7. The surgical introducer of claim 1, wherein each tip portion further comprises an L-shaped slot configured to receive the suture loop.

8. A method to secure a four-armed urethral sling comprising the steps:
   positioning a first pair of arms of a four-armed urethra sling to suitable sites in left and right transobturators of a patient; and
   positioning a second pair of arms of the four-armed urethral sling to suitable sites through the abdominal wall of the patient suprapubicly, wherein a portion of the second pair of arms is guided through the abdominal wall of the patient via a surgical introducer as claimed in claim 1.

9. A kit comprising instructions and a surgical introducer for positioning a urethral sling comprising:
   a proximal tip portion and a distal tip portion, wherein each tip portion comprises a T-shaped slot configured to receive a suture loop;
   a base portion comprising exactly one angle at approximately the midpoint of the introducer, wherein the base portion is between the proximal tip portion and the distal tip portion, wherein the exactly one angle displaces the proximal tip portion out of a plane parallel with the distal tip portion, wherein the exactly one angle is acute as measured from the horizontal plane parallel with the distal tip portion to the outside of the proximal tip portion, wherein the base portion is wider than the remainder of the introducer, and wherein the width of the introducer is from about ¼ inches to about 1 inch.

10. The kit of claim 9, wherein the instructions include a method to secure a four-armed urethral sling comprising the steps:
    positioning a first pair of arms of the four-armed urethra sling to suitable sites in the left and right transobturators of a patient; and
    positioning a second pair of arms of the four-armed urethral sling to suitable sites through the abdominal wall of the patient suprapubicly, wherein a portion of the second pair of arms is guided through the abdominal wall of the patient via the surgical introducer.

11. A surgical introducer for positioning a urethral sling comprising:
    a proximal tip portion and a distal tip portion, wherein the distal tip portion and the proximal tip portion each comprise a T-shaped slot configured to receive a suture loop and an L-shaped slot configured to receive the suture loop; and
    a substantially tubular base portion comprising exactly one angle at approximately the midpoint of the introducer, wherein the base portion is between the proximal tip portion and the distal tip portion, wherein the exactly one angle displaces the proximal tip portion out of a plane parallel with the distal tip portion, wherein the exactly one angle is approximately between about 15 and about 30 degree as measured from the horizontal plane parallel with the distal tip portion to the outside of the proximal tip portion, wherein the base portion is wider than the remainder of the introducer, wherein the length of the surgical introducer is between about 15 cm to about 25 cm, and wherein the width of the introducer is from about ¼ inches to about 1 inch.

12. The surgical introducer of claim 11, wherein the distal tip portion and the proximal tip portion are substantially flat.

* * * * *